United States Patent [19]

Stähle et al.

[11] Patent Number: 4,478,844
[45] Date of Patent: Oct. 23, 1984

[54] BRADYCARDIAC OR ANALGESIC 2-(N-(THIENYL-2-METHYL)-N-(2-FLUORO-6-METHYL-PHENYL)-AMINO)-2-IMIDAZOLINE AND SALTS THEREOF

[75] Inventors: Helmut Stähle; Herbert Köppe; Werner Kummer, all of Ingelheim, Fed. Rep. of Germany; Walter Kobinger, Vienna, Austria; Klaus Stockhaus, Bingen, Fed. Rep. of Germany

[73] Assignee: Boehringer Ingelheim KG, Ingelheim am Rhein, Fed. Rep. of Germany

[21] Appl. No.: 433,086

[22] Filed: Oct. 6, 1982

Related U.S. Application Data

[63] Continuation-in-part of Ser. No. 313,475, Oct. 21, 1981, abandoned, which is a continuation of Ser. No. 215,106, Dec. 10, 1980, abandoned.

[30] Foreign Application Priority Data

Dec. 21, 1979 [DE] Fed. Rep. of Germany ....... 2951601

[51] Int. Cl.$^3$ .................. A61K 31/415; C07D 409/12
[52] U.S. Cl. ............................. 424/273 R; 548/315; 548/348
[58] Field of Search .................... 548/348; 424/273 R

[56] References Cited

U.S. PATENT DOCUMENTS

| | | | |
|---|---|---|---|
| 3,937,717 | 2/1976 | Stahle et al. | 424/273 R X |
| 4,036,972 | 7/1977 | Stahle et al. | 424/273 R X |
| 4,215,133 | 7/1980 | Stahle et al. | 424/273 R |
| 4,239,764 | 12/1980 | Stahle et al. | 424/263 |

Primary Examiner—Richard A. Schwartz
Attorney, Agent, or Firm—Hammond & Littell, Weissenberger & Dippert

[57] ABSTRACT

Compounds of the formula

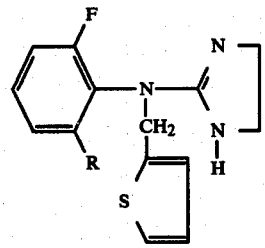

wherein R is bromine or trifluoromethyl, and non-toxic, pharmacologically acceptable acid addition salts thereof. The compounds as well as their salts are useful as bradycardiacs, analgesics and locomotion inhibitors.

3 Claims, No Drawings

BRADYCARDIAC OR ANALGESIC 2-(N-(THIENYL-2-METHYL)-N-(2-FLUORO-6-METHYL-PHENYL)-AMINO)-2-IMIDAZOLINE AND SALTS THEREOF

This is a continuation-in-part of application Ser. No. 313,475, filed Oct. 21, 1981 now abandoned; which in turn is a continuation of application Ser. No. 215,106, filed Dec. 10, 1980, now abandoned.

This invention relates to novel 2-phenylamino-2-imidazolines and non-toxic acid addition salts thereof, to a method of preparing these compounds, to pharmaceutical compositions containing them as active ingredients, and to methods of using them as bradycardiacs, analgesics and locomotion inhibitors.

More particularly, the present invention relates to a novel class of compounds represented by the formula

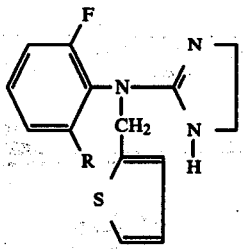

(I)

wherein R is bromine or trifluoromethyl, and non-toxic, pharmacologically acceptable acid addition salts thereof.

The compounds embraced by formula I may be prepared by reacting a 2-[(2-fluoro-phenyl)-imino]-imidazolidine of the formula

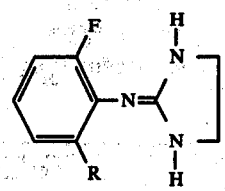

(II)

wherein R has the same meanings as in formula I, with a 2-halomethyl-thiophene of the formula

(III)

wherein Hal is chlorine, bromine or iodine.

The reaction is carried out by heating a mixture of the reactants to a temperature of 40° to 150° C., preferably in the presence of a polar or non-polar solvent.

The specific reaction conditions depend to a large extent upon the reactivity of the individual reactants. In general, it is recommended to provide the halide of the formula III in excess and to perform the reaction in the presence of an acid-binding agent.

The starting compounds of the formula II are described in the literature (see, for example, Belgian Pat. No. 623,305). The starting compounds of the formula III are obtained by halogenating the corresponding alcohols.

The compounds embraced by formula I are basic substances and therefore form addition salts with inorganic or organic acids. Examples of non-toxic, pharmacologically acceptable acid addition salts are those formed with hydrochloric acid, hydrobromic acid, hydroiodic acid, hydrofluoric acid, sulfuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxybenzoic acid, p-aminobenzoic acid, phthalic acid, cinnamic acid, salicylic acid, ascorbic acid, methane-sulfonic acid, 8-chlorotheophylline or the like.

The following examples illustrate the present invention and will enable others skilled in the art to understand it more completely. It should be understood, however, that the invention is not limited solely to the particular examples given below.

EXAMPLE 1

2-[N-(2-Fluoro-6-bromo-phenyl)-N-(thienyl-2-methyl)-amino]-2-imidazoline

A mixture consisting of 7.74 gm (0.03 mol) of 2-[(2-bromo-6-fluoro-phenyl)-imino]-imidazolidine, 5 gm (125% of the stoichiometrically required amount) of 2-chloromethylthiophene, 4.5 ml of triethylamine and 60 ml of dry toluene was refluxed for six hours while stirring. Thereafter, the precipitate which had formed was collected by suction filtration and dissolved in about 1N hydrochloric acid. The resulting solution was extracted twice with ether (the ethereal extracts were discarded), and was subsequently made alkaline with 5N sodium hydroxide. The product precipitated thereby was collected by suction filtration, washed with water and dried, yielding 6.5 gm (61.2% of theory) of the compound of the formula

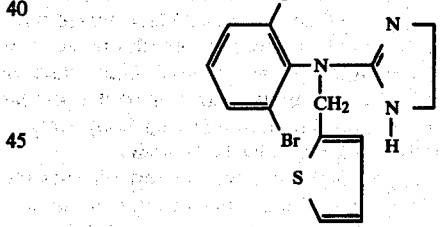

which had a melting point of 107°–108° C.

| | Element analysis $C_{14}H_{13}BrFN_3S$ (354.24) | | | | | |
|---|---|---|---|---|---|---|
| | C | H | N | Br | F | S |
| Calc: | 47.48% | 3.70% | 11.86% | 22.56% | 5.36% | 9.04% |
| Found: | 47.54% | 3.91% | 11.88% | 22.37% | 5.24% | 9.01% |

EXAMPLE 2

2-[N-(2-Fluoro-6-trifluoromethyl-phenyl)-N-(thienyl-2-methyl)-amino]-2-imidazoline This compound was prepared in analogy to Example 1, starting from 2-[(2-fluoro-6-trifluoromethyl-phenyl)-imino]imidazolidine and 2-chloromethyl-thiophene. It had a melting point of 110°–111° C. The yield was 56.3% of theory.

The compounds of the present invention, that is, those embraced by formula I above and their non-toxic, pharmacologically acceptable acid addition salts, have useful pharmacodynamic properties. More particularly, they exhibit bradycardiac analgesic and locomotion-inhibiting activities in warm-blooded animals such as mice, rats and rabbits.

The end product of Example 1, i.e. 2-[N-(2-fluoro-6-bromo-phenyl)-N-(thienyl-2-methyl)-amino]-2-imidazoline (A), and [N-2,6-dibromo-phenyl)-N-(thienyl-2-methyl)-amino]-2-imidazoline (B), disclosed in column 2, lines 47–48, of U.S. Pat. No. 3,937,717, were tested for analgesic activity and locomotion-inhibiting activity by the standard test methods described in the following literature references:

Analgesic activity: Ph. Linee, J. Pharmacol. (Paris) 3,4 513–515 (1972). Writhing test.

Locomotion—inhibiting activity: K. Stockhaus et al., Committee on Problems of Drug Dependence (1970) 6890–6898 National Academy of Sciences.

The following results were obtained.:

| Compound | Writhing test (mouse) | | Locomotion inhibition (mouse) $ED_{50}$ s.c. |
|---|---|---|---|
| | $ED_{50}$ s.c. | $ED_{50}$ p.o. | |
| A | 0.12 | 0.28 | 0.13 |
| B | 0.3 | 0.6 | 0.6 |

These results show that the compound of the present invention is twice as effective as an analgesic and four times as effective a locomotion inhibitor as the prior art compound.

For pharmaceutical purposes the compounds of the present invention are administered to warm-blooded animals perorally, parenterally or rectally as active ingredients in customary dosage unit compositions, that is, compositions in dosage unit form essentially of an inert pharmaceutical carrier and one effective dosage unit of the active ingredient, such as tablets, coated pills, capsules, wafers, powders, solutions, emulsions, suspension, syrups, suppositories and the like. One effective dosage unit of the compounds according to the present invention is from 0.0014 to 1.14 mgm/kg body weight, preferably 0.014 to 42 mgm/kg body weight.

The following examples illustrates a few pharmaceutical dosage unit compositions comprising a compound of the present invention as an active ingredient and represent the best modes contemplated of using the invention. The parts are parts by weight unless otherwise specified.

EXAMPLE 3

Coated Tablets

The tablet core composition is compounded from the following ingredients:

| | |
|---|---|
| 2-[N—(Thienyl-2-methyl)-N—(2-fluoro-6-bromo-phenyl)-amino]-2-imidazoline | 5 parts |
| Lactose | 65 parts |
| Corn starch | 130 parts |
| Sec. calcium phosphate | 40 parts |
| Soluble starch | 3 parts |
| Magnesium stearate | 3 parts |
| Collodial silicic acid | 4 parts |
| Total | 250 parts |

Preparation

The active ingredient is admixed with a portion of the excipients, the mixture is thoroughly kneaded with an aqueous solutions of the soluble starch, and the moist mass is granulated by passing it through a screen. The granulate is dried, admixed with the remainder of the excipient, and the composition is compressed into 250 mgm-tablet cores which are subsequently coated with a thin shell consisting essentially of a mixture of sugar, talcum and gum arabic. Each coated tablet is an oral dosage unit composition containing 5 mgm of the active ingredient.

EXAMPLE 4

Hypodermic solution

The solution is compounded from the following ingredients:

| | |
|---|---|
| 2-[N—(Thienyl-2-methyl)-N—(2-fluoro-6-trifluoromethyl-phenyl)-amino]-2-imidazoline | 1.0 parts |
| Sodium chloride | 18.0 parts |
| Distilled water q.s.ad | 2000.0 parts by vol. |

Preparation

The active ingredient and the sodium chloride are dissolved in the distilled water, the solution is filtered until free from suspended particles, and the filtrate is filled into 2 cc-ampules in an atmosphere of nitrogen. The contents of each ampule are an injectable dosage unit composition containing 1 mgm of the active ingredient.

EXAMPLE 5

Drop solution

The solution is compounded from the following ingredients:

| | |
|---|---|
| 2-[N—(Thienyl-2-methyl)-N—(2-fluoro-6-bromo-phenyl)-amino]-2-imidazoline | 0.02 parts |
| Methyl p-hydroxy-benzoate | 0.07 parts |
| Propyl p-hydroxy-benzoate | 0.03 parts |
| Demineralized water q.s. ad | 100 parts by vol. |

Preparation

The active ingredient and the p-hydroxy-benzoates are dissolved in the demineralized water, the resulting solution is filtered, and the filtrate is filled into 100 ml-bottles equipped with a dropping spout. 5 ml (about 20 drops) of the solution are an oral dosage unit composition containing 1 mgm of the active ingredient.

Any one of the other compounds embraced by formula I or a non-toxic, pharmacologically acceptable acid addition salt thereof may be substituted for the particular active ingredient in Examples 3 through 5. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. 2-[N-(2-Fluoro-6-bromo-phenyl)-N-(thienyl-2-methyl)-amino]-2-imidazoline or a non-toxic, pharmacologically acceptable acid addition salt thereof.

2. A bradycardiac or analgesic pharmaceutical dosage unit composition consisting essentially of an inert pharmaceutical carrier and an effective bradycardiac or analgesic amount of a compound of claim 1.

3. The method of slowing the heart rate or raising the pain threshold of a warm-blooded animal in need thereof, which comprises perorally, parenterally or rectally administering to said animal an effective bradycardiac or analgesic amount of a compound of claim 1.

* * * * *